United States Patent [19]

Lazzeri et al.

[11] Patent Number: 5,416,009
[45] Date of Patent: May 16, 1995

[54] NUCLEOTIDE MOLECULE ENCODING A SPECIFIC ONCHOCERCA VOLVULUS ANTIGEN FOR THE IMMUNODIAGNOSIS OF ONCHOCERCIASIS

[75] Inventors: Mario E. S. L. Lazzeri, Washington, D.C.; Thomas B. Nutman, Takoma Park, Md.; Niklaus Weiss, Basile, Switzerland

[73] Assignee: The United States of America, Washington, D.C.

[21] Appl. No.: 644,372

[22] Filed: Jan. 23, 1991

[51] Int. Cl.[6] .................. A61K 39/002; C07K 15/08; C12N 15/30

[52] U.S. Cl. .................................. 435/69.3; 435/4; 435/7.1; 435/7.22; 435/69.1; 435/71.1; 435/71.2; 435/172.3; 435/252.3; 435/320.1; 530/350; 536/23.1; 536/23.4; 536/23.5; 536/23.7

[58] Field of Search .............. 536/27, 23.1, 23.4, 536/23.5, 23.7; 435/320.1, 252.3, 69.1, 69.3, 4, 7.1, 7.22, 71.1, 71.2, 172.3; 424/88; 530/350

[56] References Cited

PUBLICATIONS

Hugh R. Taylor, et al., "Impact of Mass Treatment of Onchocerciasis with Ivermetcin on the Transmission of Infection", Science 250:116–118 (1990).
Niklaus Weiss et al., "Evaluation of a Specific Enzyme Immunoassay for Onchocerciasis Using a Low Molecular Weight Antigen Fraction of *Onchocerca Volvulus*", Am. J. Trop. Med. Hyg. No. 3, 40:261–267 (1989).
Richard Lucius, et al., "Molecular Cloning of an Immunodominant Antigen of *Onchocerca Volvulus*", J. Exp. Med. 168:1199–1204 (1988).
Hugh R. Taylor et al., "Invermectin Prophylaxis Against Experimental *Onchocerca Volvulus* Infection in Chimpanzees" Am. J. Trop. Med. Hyg. No. 1, 39:86–90 (1988).
Thomas R. Unnasch et al., "Isolation and Characterization of Expression cDNA Clones Encoding Antigens of *Onchocerca Volvulus* Infective Larvae", J. Clin. Invest. 82:262–269 (Jul. 1988).
John E. Donelson et al., "Construction of *Onchocerca Volvulus* cDNA libraries and Partial Characterization of the cDNA for a Major Antigen", Mol. Biochem. Parasitol., 31:241–250 (1988).
Zully Cabrera et al., "Identification of Antigens of *Onchocerca Volvulus* and *Onchocerca Gibsoni* for Diagnostic Use", Mol. Biochem. Parasitol., 20:225–231 (1986).
Niklaus Weiss et al., "Humoral Immune Responses in Human Onchocerciasis: Detection of Serum Antibodies in Early Infections", Ciba Found. Symp. 27:180–188 (1987).
World Health Organization, Technical Report Series (WHO Expert Committee on Onchocerciasis, 3rd Report), No. 752, WHO, Geneva (1987).
M. A. Aziz, "Ivermectin vs. Onchocerciasis", Parasitology Today, 2(9):233–235 (Sep. 1986).
J. Walsh, "River Blindness: A Gamble Pays Off", Science 232:922–925 (May 23, 1986).
E. Lobos et al., "Identification of Non–crossreacting Antigens of *Onchocerca Volvulus* With Lymphatic Filariasis Serum Pools", Parasitology, 93:389–399 (1986).
Marc Karam et al., "Seroepidemiological Investigations of Onchoerciasis in a Hyperendemic Area of West Africa", Am. J. Trop. Med. Hyg., 34(5):907–917 (1985).

(List continued on next page.)

Primary Examiner—Christine M. Nucker
Assistant Examiner—Michael Tuscan
Attorney, Agent, or Firm—Needle & Rosenberg

[57] ABSTRACT

The present invention relates to a DNA segment encoding an *Onchocerca volvulus* antigen: a specific and early marker of onchocerciasis infection. The nvention further relates to recombinant molecules containing such a segment and to methods of utilizing same to produce the *Onchocerca volvulus* antigen. The invention also relates to the antigen itself. The invention further relates to methods of diagnosing Onchocerciasis infection.

11 Claims, 11 Drawing Sheets

OTHER PUBLICATIONS

N. A. Kaushal et al., "Excretory-secretory and Somatic Antigens in the Diagnosis of Human Filariasis", *Clin. Exp. Immunol.*, 56:567–576 (1984).

H. Schulz-Key et al., "Isolation of Living Adult *Onchocerca Volvulus* From Nodules", *Tropenmed. Parasitol.*, 28:428–430 (1977).

Pierre Ambroise-Thomas, "Immunological Diagnosis of Human Filariasis: Present Possibilities, Difficulties and Limitations", *Acta Trop.* 31:108–128 (1974).

Gallin, M. Y. et al. (1987) J. Inf. Dis. 160:521–529.

Lobos E. et al. (1990) Med. Biochem. Parasitol. 39:135–146.

Dinman, J. D. et al. (1990) Exp. Parasitol. 71:176–188 (abstract only provided).

Corina, K. F. et al. (1990) J. Immunol. 145:1551–1556.

Maiha, C. V. (1988) Gene 74:365–373.

Young, R. A. et al. (1983) Proc. Natl. Acad. Sci. USA 80:1194–1198.

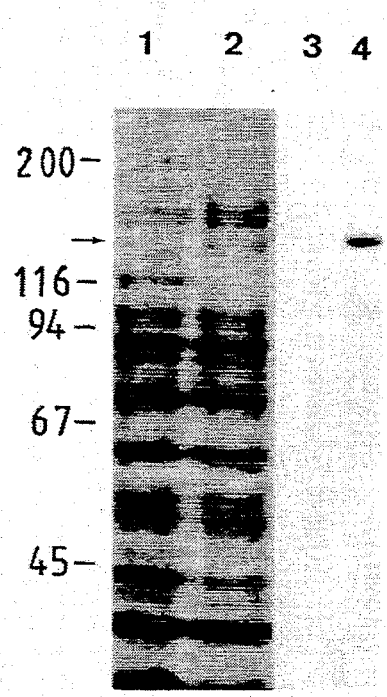
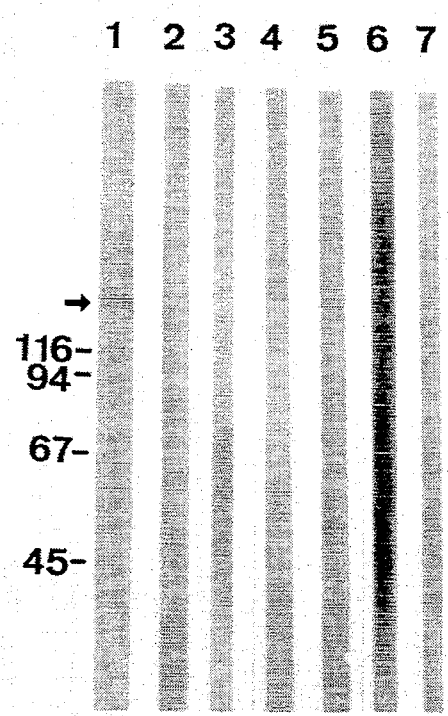
FIGURE 2A
FIGURE 2B

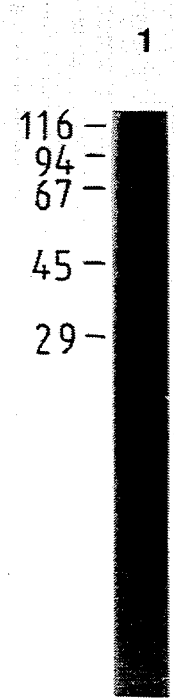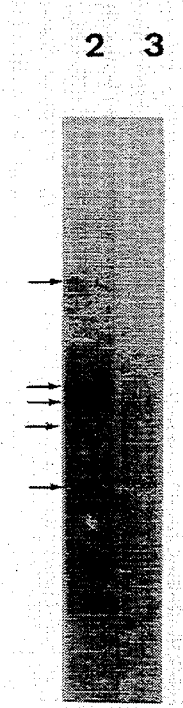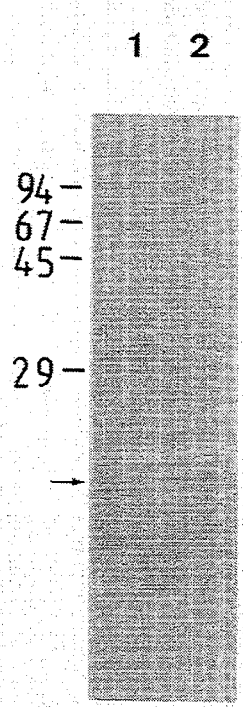
FIGURE 3A  FIGURE 3B

EcoRI LINKER
```
                                                                                  Met His Cys
         1
GAA TTC  CAG TTT GAG GAT CGG TTG CTT GTT TTT TGC ATC AAT CGT GTA TGC TCG ATA ATG CAT TGT
         61
         Leu Gln Val Val Ile Ala Ile Val Leu Tyr Ser Phe Gly Lys Ile Ser Ala Glu Asn Ala
         TTG CAA GTA GTA ATC GCC ATA GTA TTG TAC TCA TTT GGA AAA ATA TCT GCA GAA AAT GCT
         121                 ▼
         Asn Cys Lys Lys Cys Thr Pro Met Leu Val Asp Ser Ala Phe Lys Glu His Gly Ile Val
         AAT TGC AAA AAG TGC ACA CCA ATG TTA GTA GAT TCG GCA TTC AAG GAA CAT GGA ATT GTA
         181
         Pro Asp Val Val Ser Thr Ala Pro Thr Lys Leu Val |Asn Val Ser|Tyr Asn|Asn Leu Thr|
         CCG GAC GTT GTA TCA ACA GCT CCT ACG AAG TTG GTC|AAT GTT AGT|TAC AAT|AAT CTC ACG|
         241
         Val Asn Leu Gly Asn Glu Leu Thr Pro Thr Gln Val Lys Asn Gln Pro Thr Lys Val Ser
         GTG AAT CTG GGC AAT GAA CTT ACG CCG ACG CAG GTA AAG AAT CAG CCG ACA AAA GTA TCA
         301
         Trp Asp Ala Glu Pro Gly Ala Leu Tyr Thr Leu Val Met Thr Asp Pro Asp Ala Pro Ser
         TGG GAT GCG GAA CCT GGA GCC TTA TAT ACG CTC GTT ATG ACT GAT CCG GAC GCA CCA TCT
         361
         Arg Lys Asn Pro Val Phe Arg Glu Trp His His Trp Leu Ile Ile |Asn Ile Ser|Gly Gln
         CGA AAA AAC CCC GTA TTC AGA GAG TGG CAC CAT TGG TTG ATA ATT |AAT ATT TCT|GGA CAA
         421
         |Asn Val Ser|Ser Gly Thr Val Leu Ser Asp Tyr Trp Ile Arg Ser Thr Lys Arg His Arg
         |AAT GTT AGC|AGT GGC ACA GTG TTA TCT GAT TAT TGG ATC AGG TCC ACG AAA AGG CAC AGG
         481                                 511
         Thr Ser Ser Leu Cys Ile Leu Gly Leu ***
         ACT TCA TCG TTA TGT ATT CTT GGT TTA TAA ACA ACC TGG AAG TAT CAC GGA TAC TCA ACA
         541
         TGG CGG AAA TCG CCG AAA TTT CAA AGT TAT GGA TTT TGC AAA CAA ACA TCA CTT GGG AAA
         601
         TCC AGT TGC CGG AAA CTT CTT CCA GGC TAA ACA TGA GGA TTA ACA TGA AGA CTG TGA ATA
         661
         TGA ATA TGA ACT GCT TGA ACG ACA CTA GAG ACT CAG CGA CTG ATA CTT ATT GAT TTG TTT
         721
         TTG TAA CAT TTG AAT GAA TTT TTC TTT ACA GTT ATT TGC TAA ATT TCG AAT TTA ATG GGA
         781
         ATA AAT ATT TTT TAA AAA AAA AAA AAA AAA AAA AGGAATTCC
```

FIGURE 4A

NUCLEOTIDE MOLECULE ENCODING A SPECIFIC ONCHOCERCA VOLVULUS ANTIGEN FOR THE IMMUNODIA absence of parasite RNA; lane 2, total translation products from savanna *O. volvulus*. Immunoprecipitation of in vitro translated polypeptides using: lane 3, normal human serum pool (NHS pool); lane 4, lymphatic filariasis serum pool from India (F-I); lane 5, lymphatic filariasis serum pool from the Philippines (F-P); lane 6, onchocerciasis serum pool from Mali (O.V.-M.); and lane 7, onchocerciasis serum pool from Tanzania (O.V.-T). Lane 8, loiasis serum pool from Congo (F-L); lane 9, *M. perstans serum* pool (F-M) from West Africa; lane 10, intestinal nematodes serum pool (I-N). Numbers on the right indicate size of molecular weight markers in kDa. See text for details.

FIG. 2A–2B. (A) Characterization of the fusion protein encoded by OV-16 cDNA. SDS-PAGE analysis of extracts of *E. coli* Y1090 cells infected with gtll (lane 1) or clone OV-16 cDNA (lane 2), and Western blot of the same extracts incubated with anti-20-42K antibodies (lanes 3 and 4). Arrow indicates the position of the fusion protein at 134 kDa. (B) Western blots incubated with affinity-purified antibodies from onchocerciasis patients or other filarial and non-filarial serum pools. Extracts of *E. coli* Y1090 (approximately 80 µg) infected with the recombinant phage OV-16 were fractionated by 7.5% SDS-PAGE and blotted onto nitrocellulose filters. Lane 1 was incubated with affinity-purified antibodies from onchocerciasis patients. Lanes 2 and 3 were incubated with filariasis serum pools from India and the Philippines, respectively; lanes 4, 5, and 6 were incubated with serum pools from patients infected with *L. loa, M. perstans,* or intestinal nematodes; lane 7 was incubated with normal serum pool. Molecular weight markers are indicated on the left.

FIG. 3A–3B. (A) Identification of the native parasite proteins that are antigenic determinants with the OV-16 cDNA fusion protein. SDS-PAGE analysis of *O. volvulus* proteins (approximately 80 µg) (lane 1) and Western blot probed with antibody selected against the OV-16 cDNA fusion protein (lane 2); lane 3 is a control using HRPO rabbit anti-human IgG (heavy chain); the band running at 50 kDa (asterisk) is the heavy chain of human IgG present in the parasite extract. (B) Identification of the primary translation product of the *O. volvulus* antigen mRNA. Total parasite proteins synthesized by in vitro translation of parasite RNA were immunoprecipitated with affinity-purified antibody against β-galactosidase (lane 1) or the OV-16 cDNA fusion protein 9 (lane 2). Immunoprecipitation of [$^{35}$S]methionine-labeled in vitro translated proteins were carried out using 30 µl of antibody selected against the recombinant antigen and 10 µl of rabbit anti-human IgG. Immunoprecipitates were electrophoresed on a 17.5% SDS-poly-acrylamide gel, processed for fluorography, dried, and autoradiographed.

FIG. 4A–4B. (A) Nucleotide sequence and predicted amino acid sequence of the OV-16 cDNA. (SEQ ID NO:I and SEQ ID NO:2) Arrowhead, 5' end of the OV-16' cDNA clone. The OV-16' cDNA and OV-16 cDNA EcoRI fragments were subcloned into M13mp18 in both orientations. Internal fragments were obtained by Sau3A restriction enzyme digestion and ligation into the BamHI site of M13mp18. Sequence determination was carried out by the chain termination method (Sanger et al. (1977) Proc. Natl. Acad. Sci. USA 74, 5463–5467). The following subclones from the coding strand were sequenced: EcoRI fragment, nucleotides 1–320; Sau3A fragments, 341–457, 454–686; EcoRI/Sau3A fragment, 1–344; from the non-coding sequence: EcoRI fragment 812–490; Sau3A fragments 686–454, 457–341. The putative signal sequence is underlined. Four potential N-linked glycosylation sites, boxed. The proposed consensus polyadenylation signal AATAAA is doubly underlined. (B) Analysis of the hydropathy of OV-16 cDNA by the procedure of Kyte and Doolittle. Hydropathy values were averaged for a window of 10 amino acid residues. Positive numbers, hydrophobicity; negative numbers, hydrophilicity.

FIG. 5. Left-hand panel: parasite sequences hybridizing to the OV-16 cDNA insert 1. Southern blot analysis of genomic DNA from *O. volvulus* by OV-16 cDNA. EcoRI digest (lane a), HindIII digest (lane b). Markers are HindIII fragments of $I_{857}$ (kb). Right-hand panel: Northern blot analysis of total RNA from *O. volvulus* hybridized to OV-16 cDNA; markers are calf liver 18S and 28S RNA.

FIG. 6. Ultrastructural localization by immunoelectron microscopy of parasite antigens that share antigenic determinants with the OV-16 cDNA fusion protein. (1) Hypodermis (h); (2) cortical layer of the cuticle (cl); (3) apical part and surface of the uterine epithelium (ue). First two magnifications x44850; the third, x17940. Immunocytochemistry was carried out on thin sections of *O. volvulus* worms prepared from electron microscopy using the low-temperature embedding technique in Lowicryl K4M. Thin sections were incubated with antibody selected against the OV-16 cDNA recombinant antigen and subsequently with goat anti-human IgG coupled to 9-nm gold particles for indirect antigen localization.

FIG. 7. Construction of pCG808fx OV-16. The recombinant plasmid was obtained by ligating a 682 bp fragment of OV-16 (H. R. Taylor et al., Science 250,116 (1990)) into the EcoRI site of pCG808fx (C. V. Maina et al., Gene 74,365 (1988)). This plasmid contains a portion of the malE gene with its signal sequence fused to the Lac Z coding sequence; fx denotes the recognition site for factor Xa. The ligation mixture was used to transform *E. coli* 71–18. Transformants expressing the *O. volvulus* OV-16 antigen were identified by Western blotting using a pool of sera from patients with onchocerciasis.

FIG. 8A–8B. Panel A: SDS-PAGE analysis of the expression and isolation of the *O. volvulus* antigen as a MBP-16 fusion protein and the subsequent separation of the protein domains. Samples subjected to SDS-PAGE (5/15% gradient gels) were 40 µg *E. coli* lysate before induction (lane 1), 40 µg cell lysate after induction (lane 2), 40 µg flow-through from an amylose column (lane 3), 5 µg purified MBP-16 eluted from the cross-linked amylose column (lane 4), and 5 µg MBP-16 after digestion with factor $X_a$ for 4 days at r.t. (lane 5). Molecular size standards were from Amersham. Panel B: Western blot analysis of the isolated *O. volvulus* antigen (OV-16). Identical gels (4/20% gradient with 5 µg MBP-16 (lanes 1 and 4), 5 µg fx$_a$-digested MBP-16 (lanes 2 and 5), and 200 ng of the FPLC-isolated OV-16 (lanes 3 and 6) were blotted onto nitrocellulose. They were probed with rabbit antiserum raised against MBP (1:20,000) (lanes 1, 2, and 3) or with a pool of sera from patients with onchocerciasis (lanes 4, 5, and 6 [1:500]). Bound antibodies were visualized by a second incubation with alkaline phosphatase-conjugated goat antibody to rabbit or human IgG.

FIG. 9. Detection of *O. volvulus*-specific antibodies (total IgG) onchocerciasis patients by means of the recombinant OV-16 antigen in ELISA (11). Sera from clinically well-defined filarial infections including *M. ozzardi* (N=5), *M. perstans* (N=2), *L. loa* (N=14), as well as patients with lymphatic filariasis caused by *W. bancrofti* (N=25) or *B. malayi* (N=12). The dotted line represents the cut-off values calculated as the mean of the control sera (N=13) plus three standard deviations.

FIG. 10A-10B. Seroreactivity against OV-16 in experimental *O. volvulus* infection in chimpanzees. Each animal was inoculated with 250±5 infective third-stage ($L_3$) larvae of *O. volvulus*. Detailed parasitological examinations were carried out monthly from three months before inoculation until 38 months postinoculation (H. R. Taylor et al., Am. J. Trop. Med. Hyg. 39,86 (1988)). ELISA was carried out. Chimpanzees showed a positive titer against OV-16 three months (A) and 12 months (B) prior to the time that mf were first detected in the skin.

DETAILED DESCRIPTION OF THE INVENTION

Figure 1:
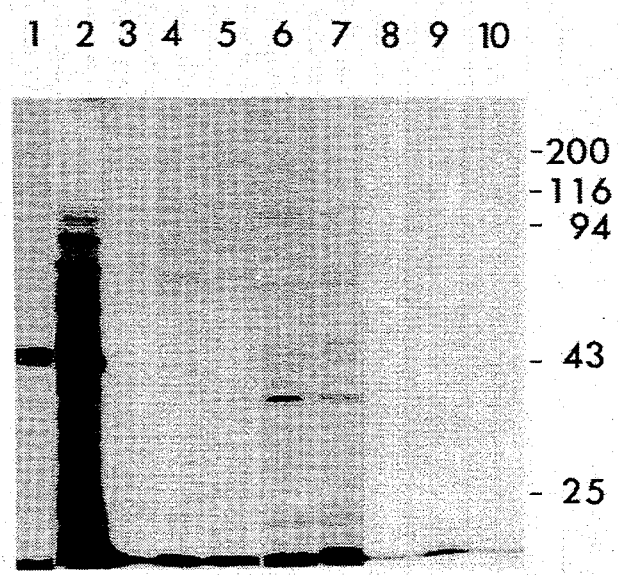

The present invention relates, in part, to a DNA segment coding for a polypeptide having an amino acid sequence corresponding to a low molecular weight antigen uniquely recognized by antibodies present in onchocerciasis patient sera.

More specifically, the present invention relates to a DNA segment coding for a polypeptide having an amino acid sequence corresponding to OV-16. In one embodiment, the DNA segment has the sequence shown in FIG. 4, or allelic or species variation thereof, or a unique portion of such a sequence (unique portion being defined herein as at least 15–18 bases); complements of such sequences are also within the scope of the present invention. In another embodiment, the DNA segment encodes the amino acid sequence shown in FIG. 4, or allelic or species variation thereof or a unique portion of such a DNA sequence. In another embodiment, the DNA segment encodes amino acids 30 to 152 shown in FIG. 4 (amino acid 30 being immediately preceeded by an arrow), or allelic or species variation thereof or a unique portion of such a DNA sequence.

In another embodiment, the present invention relates to a polypeptide having an amino acid sequence corresponding to a low molecular weight antigen uniquely recognized by antibody present in onchocerciasis patient sera and either free of proteins with which it is naturally associated or bound to a solid support. In a specific embodiment, the polypeptide has an amino acid sequence corresponding to OV-16. In one preferred embodiment, the polypeptide has the amino acid sequence as shown in FIG. 4, or allelic or species variation thereof, or a unique portion of such sequences (unique portion being defined herein as at least 5–6 amino acids). In another preferred embodiment, the polypeptide has amino acids 30 to 152 shown in FIG. 4, or allelic or species variation thereof, or a unique portion of such sequences as defined above.

In another embodiment, the present invention relates to a recombinant DNA molecule comprising a vector (for example—plasmid or viral vector) and the DNA segment coding for a low molecular weight antigen uniquely recognized by antibody present in onchocerciasis patient sera or the OV-16 polypeptide or amino acids 30 to 152 of the OV-16 polypeptide (amino acid 30 being immediately preceeded by an arrow), as described above. In a preferred embodiment, the encoding segment is present in the vector operably linked to a promoter. In another preferred embodiment, the present invention relates to the recombinant DNA molecule pCG808fx-16.

In a further embodiment, the present invention relates to a cell containing the above described recombinant DNA molecule. Suitable host cells include procaryotes (such as bacteria, including *E. coli*) and both lower eucaryotes (for example yeast) and higher eucaryotes (for example, mammalian cells). Introduction of the recombinant molecule into the host cell can be effected using methods known in the art.

In another embodiment, the present invention relates to a method of producing the above described polypeptides, comprising culturing the above described host cells under conditions such that the polypeptide is produced, and isolating the polypeptide.

In another embodiment, the present invention relates to a method of diagnosing onchocerciasis in an animal comprising (1) contacting serum from the animal with a low molecular weight antigen uniquely recognized by onchocerciasis patient sera under conditions such that binding of the antigen with an antibody in the serum can be effected, whereby a compound is formed and (2) detecting the compound. In a further embodiment, the present invention relates to a method of diagnosing onchocerciasis in an animal comprising (1) contacting serum from the animal with OV-16 protein under conditions such that binding of the antigen with an antibody in the serum can be effected, whereby a compound is formed and (2) detecting the compound.

The use of recombinant antigen OV-16 overcomes many of the problems that previously plagued the diagnosis of onchocerciasis: lack of parasite material, poor specificity and sensitivity of the assays, and insensitivity for detecting prepatent and low level infections. Over most of the large area of the onchocerciasis Control Program in West Africa, *O. volvulus* transmission has been interrupted by vector control (J. Walsh, Science 232,922 (1986)). However, reinvasion of infective black flies occurs in some border areas and is responsible both for recurrent infections (WHO. Technical Report Series. No. 597. WHO Geneva (1976)) and for infections of children previously unexposed (born after the establishment of effective vector control). The use of OV-16, or of similar specific immunodominant antigens, should allow the early and specific diagnosis of new or reinfections with *O. volvulus* in such vector reinvasion areas, as well as the detection of light infections in areas where control is being attempted by widespread use of ivermectin (M. A. Aziz, Parasitol. Today 2, 233 (1986)). Such capability will be of paramount importance in monitoring, evaluating and consolidating onchocerciasis control by both the vector control and chemotherapeutic strategies.

The present invention is described in further detail in the following non-limiting examples.

EXAMPLES

The following protocols and experimental details are referenced in the Examples that follow:

Parasites. Nodulectomy of onchocerciasis patients was performed in Manambougou (12°45'N, 7°40'W), a small village 30 km north-east of Bamako (Republic of Mali) located on the bank of the Niger River. *O. volvulus* worms (savanna form) were recovered from these nodules after digesting by collagenase as described by Schulz-Key et al. (Schulz-Key et al. (1977). Tropenmed. Parasitol. 28, 428–430). Isolated worm were maintained in culture in RPMI-1640 medium (gentamicin 50mg ml$^{-1}$, penicillin 100,000 U ml$^{-1}$) for 2 days. Only intact and motile filariae were selected and frozen in liquid nitrogen.

Isolation of parasite RNA and DNA. The RNA was extracted from 26 frozen filarial worms by grinding to a paste in a mortar according to the hot phenol method (Maniatis et al. (1982) Molecular Cloning. A Laboratory, Manual. Cold Spring Harbor Laboratory, Cold Spring Harbor, N.Y.), using a 1:1 mixture of phenol and LiDS buffer (20 mM Tris, pH 7.5/200 mM LiCl/2 mM Li-EDTA/1% lithium dodecyl sulfate(LiDS)). 860μg total RNA was obtained from the female worms. *O. volvulus* genomic DNA was prepared from 3 frozen filarial worms after grinding them to a paste. The frozen powder was thawed and digested in 100 mM Tris, pH 8.5/50 mM Li-EDTA/200 mM LiCl/1% LIDS/200 μg proteinase K per ml at 37° C. for 1 h. The viscous solution was extracted three times with phenol at 5° C. and once with chloroform. The DNA was then prepared according to Maniatis et al. ((1982) Molecular Cloning. A Laboratory, Manual. Cold Spring Harbor Laboratory, Cold Spring Harbor, N.Y.). A total of 26 μg DNA was obtained from the filarial worms.

Isolation of Human DNA. HeLa cells were grown in suspension in Joklik-modified minimal essential medium (Gibco) containing 10% newborn calf serum. HeLa cells (about 5×10$^7$ cells) were pelleted (200 x g, 10 min, 4° C.) and washed once with cold TBS (Tris-HCl-buffered saline; 10 mM Tris-HCl, pH 7.6, 150 mM NaCl), and DNA extracted as already described (Maniatis et al. (1982) Molecular Cloning. A Laboratory, Manual. Cold Spring Harbor Laboratory, Cold Spring Harbor, N.Y.).

Cell-free synthesis and immunoprecipitation of the in vitro translated polypeptides. Cell-free protein synthesis was carried out in a mRNA-dependent rabbit reticulocyte lysate using a 20 μl incubation mixture prepared as described by Pelham and Jackson (Pelham, H. R. B. and Jackson, R. J. (1976) Eur. J. Biochem. 67,247–256), using 10 μg total filarial RNA, [$^{35}$S]methionine to 0.29 μCi || 1$^{-1}$ (1000 Ci mM$^{-1}$), and 1 h incubation at 30° C. The $^{35}$S-labeled translation products were diluted to 100 μl with immunoprecipitation buffer (Pelham, H. R. B. and Jackson, R. J. (1976) Eur. J. Biochem. 67, 247–256), the clarified labeled products (1.48×10$^5$ acid-insoluble cpm) were then immunoprecipitated with the appropriate amount of antibody, as already described (E. Lobos and N. Weiss (1986) Parasitology 93, 389–399), and analyzed directly by SDS-polyacrylamide gel electrophoresis and fluorography (Laemmli, U. K. (1970) Nature 227, 680–685; Chamberlain, J. P. (1970) Anal. Biochem. 98, 132–135).

Sera. The onchocerciasis serum pool from Mali (O.V.-M), Tanzania (O.V.-T) and the lymphatic filariasis serum pool from India (F-I) have been previously described (E. Lobos and N. Weiss (1986) Parasitology 93,389–399). The serum pool from the Philippines (F-P) consisted of 16 sera from asymptomatic microfilaremic *Wucherereia bancrofti* patients. No intestinal nematodes were detected. The loiasis serum pool (F-L) was prepared from 6 individuals from Congo with parasitologically proven *Loa loa* infection. No intestinal nematodes were detected. The *Mansonella perstans* serum pool (F-M) consisted of 6 sera from people living in different West African countries with parasitologically proven *M. perstans* infection. Three of them had *Trichuris trichiura*. The intestinal nematode serum pool (I-N) was prepared from 12 Swiss patients with parasitologically proven *Ascaris lumbricoides* and/or *T. trichiura* and who had never been exposed to any human filarial parasite. The normal human serum pool (NHS) was prepared from 6 individuals with no known parasitic infection.

Construction of a cDNA library in gt11. cDNA was synthesized with reverse transcriptase (Super RT, Stehelin, Basel, Switzerland) and oligo-dT primers followed by RNase H (Pharmacia, Uppsala, Sweden) and DNA polymerase I (New England BioLabs, Beverly, Mass.) treatment as described (Gubler, V. and Hoffman, B. (1982) Gene 25, 263–269). Treatment of double-stranded cDNA with S1 nuclease was carried out as recommended (Lapeyre, B. and Amalric, F. (1985) Gene 37, 215–220). The cDNA was methylated with EcoRI methylase, then blunt-end ligated to kinased EcoRI linkers and digested with EcoRI restriction endonuclease (all enzymes from New England Bio-Labs). The cDNA was size fractionated in a Bio-Gel A-15M column (Bio-Rad, Richmond, Calif.). Fractions containing cDNA longer than 300 bp were pooled and precipitated with isopropanol. The cDNA was ligated to EcoRI-cut and dephosphorylated gt11 vector (Young, R. A. and Davis, R. W. (1983) Proc. Natl. Acad. Sci. USA 80, 1194–1198) in the presence of 15% polyethylene glycol (PEG) (Pheiffer, B. H. and Zimmermann, S. B. (1983) Nucleic Acids Res. 11, 7853–7871). The resulting ligating products were packaged in vitro in phage gt11 using extracts and procedures described elsewhere (Maniatis et al. (1982) Molecular Cloning. A Laboratory, Manual. Cold Spring Harbor Laboratory, Cold Spring Harbor, N.Y.). The resulting library had 4×10$^6$ recombinant phage, and approximately 95% of the phage contained inserts.

Affinity purification of antibodies. SDS-treated protein extract of *O. volvulus* from Mali (800 μg) was fractionated on a preparative 12.5% SDS-polyacrylamide gel and Western-blotted as described (Towbin et al. (1979) Proc. Natl. Acad. Sci. USA 76, 4350–4354). The region of nitrocellulose between 20–42 kDA was excised and the remaining binding sites blocked with 2.5% bovine serum albumin (BSA), TBS, pH 7.5. The nitrocellulose strips were reacted overnight at 4° C. in 3 ml serum pool of onchocerciasis patients from a hyperendemic savanna region in Mali (O.V.-M) diluted 1:50 in 0.5% BSA, TBS. After 7 washes in TBS, bound antibody was then eluted by a 2-min rinse with 0.15 M glycine-Cl, pH 2.8. The eluate was quickly neutralized with 0.1 M NaOH, and BSA was added to a 0.5% concentration. These affinity-purified antibodies were used for immuno-screening of the *O. volvulus* cDNA library. Nitrocellulose strips containing 150 μg of the fusion protein transferred from 7.5% SDS-polyacrylamide gel were used to affinity purify antibody as already described (Altmann et al. (1987) Mol. Cell. Biol. 7, 998–1003). These selected antibodies were used to identify the native parasite proteins and the primary translation product, and to establish the subcellular localization of the native parasite antigens.

Immunoscreening. Immunoscreening of the gt11 cDNA library was as described with *Escherichia coli* Y1090 (Altmann et al. (1987) Mol. Cell. Biol. 7, 998–1003). After induction of the lacZ operon, the filters were saturated and incubated overnight with the affinity-purified anti-*O. volvulus* antibodies. The filters were washed for 1 h in TBS and incubated with [$^{125}$I]-protein A (10 mCi mg$^{-1}$ protein, 0.3 μCi ml$^{-1}$) in TBS for 30 min. Filters were washed for 1 h with TBS, dried, and exposed to Kodak XAR-5 film using intensifying screens. Good signals were obtained after 3-day exposure at −70° C.

DNA analysis of immunoreactive phage. Phage was amplified in *E. coli* Y1088 on plates and purified by DEAE cellulose chromatography, and their DNA was extracted (Helms et al. (1985) DNA 4, 39–49), To determine the size of the cDNA inserts, total DNA was cut with the restriction enzyme EcoRI. Fragments were separated by agarose gel electrophoresis.

DNA Sequencing. The isolated OV-16 cDNA EcoRI fragment was subcloned into M13mp18 in both orientations. Internal fragments were obtained by Sau3A restriction enzyme digestion and ligation into the BamHI site of M13mp18. Sequence determination was carried out by the chain termination method (Sanger et al. (1977) Proc. Natl. Acad. Sci. USA 74, 5463–5467).

Production of β-galactosidase-hybrid protein. *E. coli* strain Y1090 was infected with the recombinant phage on plates to achieve confluent lysis and the synthesis of protein sequences encoded by cDNA inserts was induced as already described (Young, R. A. and Davis, R. W. (1983) Science 222, 778–782). Plates were then washed (Altmann et al. (1987) Mol. Cell. Biol. 7, 998–1003) and proteins in the wash solution were concentrated by ammonium sulphate precipitation (50% saturation) and dissolved in SDS-sample buffer.

Immunoblot analysis. Polypeptides were fractionated on 7.5% or 12.5% SDS-polyacrylamide gels and transferred to nitrocellulose (Towbin et al. (1979) Proc. Natl. Acad. Sci. USA 76, 4350–4354). Nitrocellulose sheets were then reacted with the different filarial antisera (diluted 1:50 in 0.5% BSA, TBS) and bound antibody detected with peroxidase-conjugated rabbit anti-human IgG (Dako-Patts, Denmark) or using [$^{125}$I] protein A as described for the immunoscreening.

Hybridization assays. Parasite or human DNA (1 μg) was cut with restriction endonucleases and digestion products electrophoresed on a 1% agarose gel. The DNA was transferred to nitrocellulose (Southern, E. M. (1975) J. Mol. Biol 98, 503–517) and the filter baked in vacuo, hybridized in 6 x standard salt citrate (SSC), 0.5% SDS, 5 x Denhardt's 100 μg ml$^{-1}$ salmon sperm DNA. The purified OV-16 cDNA insert was labeled by nick translation and hybridized to the filter, 10$^6$ cpm ml$^{-1}$ at 68° C. The filter was washed twice in 2 x SSC, 0.5% SDS at room temperature, and twice in 0.1 x SSC, 0.5% SDS at 65° C., then autoradiographed. For Northern blot analysis, 20 g total RNA from female *O. volvulus* was denatured with glyoxal (McMaster, G. K. and Gordon, C. G. (1977) Proc. Natl. Acad. Sci. USA 74, 4835–4838), electrophoresed on a 1.5% agarose gel, blotted to nitrocellulose (Thomas, P. S. (1983) Methods Enzymol. 100, 255–266), hybridized with nick-translated OV-16 cDNA insert, 3×10$^6$ cpm ml$^{-1}$, and washed as already described.

Immunocytochemistry. Female *O. volvulus* worms isolated by the collagenase technique (Schulz-Key et al. (1977). Tropenmed. Parasitol. 28, 428–430) were fixed in 0.5% (v/v) glutaraldehyde in 0.1 M phosphate-buffered saline (PBS), pH 7.2, and maintained in 0.1 M PBS. Dehydration with graded ethanol and penetration with Lowicryl K4M were accomplished using a low-temperature embedding technique (Kellenberger et al. (1980) Chemische Werke Lowi GmbH, Wald Kraiburg, F.R.G.).

Immunocytochemistry was carried out using antibody selected against the OV-16 cDNA recombinant antigen followed by goat anti-human IgG coupled to 9 nm gold particles (DeMey, J. (1983) Immuno-gold staining of surface cell antigens in cell suspensions. GAMG 30/colloidal gold coated with immunoglobulins. Jansen Life Science Products Division, Belgium) for antigen localization.

EXAMPLE 1

Immunoprecipatation of Translated *O. volvulus* Antigens

To ensure that the RNA isolated from the female *O. volvulus* was intact, mRNA in vitro translation was carried out using rabbit reticulocyte lysate, and the [$^{35}$S]methionine-labeled products were analyzed SDS-PAGE and fluorography (FIG. 1). When 10 μg of total RNA from *O. volvulus* was added to the system, at least 50 $^{35}$S-labeled polypeptides could be detected (FIG. 1, lane 2), ranging from 14–200 kDa, indicating that the RNA isolated from the filariae was sufficiently intact to act as a template in a message-dependent cell-free system. When those $^{35}$S-labeled translation products were immunoprecipitated with the onchocerciasis serum pool from Mali (O.V.-M), 16 different antigens or antigen complexes could be detected (lane 6) ranging from 20 to 104 kDa. The cross-reactivity between the in vitro translated products and the serum pools from patients infected with other filarial parasites (*W. bancrofti, L. loa, M. perstans*) or with intestinal nematodes (*A. lumbricoides, T. trichiura*) was minimal (FIG. 1, lanes 4, 5, 8, 9 and 10).

Immunoprecipitation of the in vitro-translated polypeptides using onchocerciasis serum pools (FIG. 1, lanes 6 and 7) indicated that there are many *O. volvulus* polypeptides that do not require further processing and/or post-translational modifications to attain their antigenicity. Although the lymphatic filariasis, loiasis, mansonellosis and intestinal nematode serum pools have been previously shown to cross-react widely with native *O. volvulus* antigen (E. Lobos and N. Weiss (1986) Parasitology 93, 389–399; Weiss, N. and Karam, M. (1989) Am. J. Trop. Med. Hyg. 40, 261–267), there was relatively little cross-reactivity of these in vitro translated proteins when reacted with these sera.

EXAMPLE 2

Isolation of OV-16 cDNA Clone

To develop a cDNA library, 10 μg of the total RNA from microfilaria-producing female *O. volvulus* were used to synthesize cDNA as described (Lapeyre, B. and Amalric, F. (1985) Gene 37, 215–20). The resulting library containing approximately 4.1×10$^6$ recombinants with an average insert size of 1.1 kb.

Approximately 300,000 recombinant clones were screened with antibodies affinity-purified from a serum pool from West African onchocerciasis patients (O.V.-M pool). Of the 14 clones identified, the OV-16 cDNA clone was used for further characterization because of the strong antibody response to it. This clone was further characterized by preparing lysates from infected cells that were analyzed by Western blotting to identify the immunoreactive protein with the affinity-purified antisera. The OV-16 cDNA clone was shown to be producing a hybrid protein of 134 kDa, (thus about 18 kDa large than β-galactosidase; FIG. 2A, lane 2). The fusion protein reacted strongly on Western blots, not only with these affinity-purified antibodies (FIG. 2A, lane 4), but also with each of the eight individual sera of which the pool was made up (data not shown).

The recombinant antigen also showed striking species specificity (FIG. 2B); it did not react with serum pools obtained from patients infected with lymphatic filariae (*W. bancrofti*), with other filariae (*L. loa, M. perstans*), or with intestinal nematodes (*A. lumbricoides, T. trichiura*).

EXAMPLE 3

Identification of the Native Parasite Proteins and of the Primary Translation Products To identify the native *O. volvulus* protein(s) that share antigenic determinants with the OV-16 cDNA fusion protein, the hybrid protein was bound to nitrocellulose and used to affinity purify antibodies from the onchocerciasis serum pool (O.V.-M). Immunoblot analysis with the selected antibodies detected 2 polypeptides strongly (24 and 26 kDa) and 3 weakly (17, 22 and 40 kDa) (FIG. 3A, lane 2).

To examine the possibility that the protein encoded by the OV-16 cDNA might be modified in vivo and to identify the primary translation product of the OV-16 cDNA mRNA, [$^{35}$S]methionine-labeled cell-free translation products were subjected to immunoprecipitation with antibody selected against the parasite epitopes encoded by OV-16 cDNA. As shown in FIG. 3B, lane 2, a polypeptide of 18 kDa was specifically immunoprecipitated. In contrast, the band was not present when antibodies selected against β-galactosidase alone were used as a control (lane 1).

EXAMPLE 4

Characterization of the OV-16 cDNA Clone and cDNA Sequence

Figure 4B:
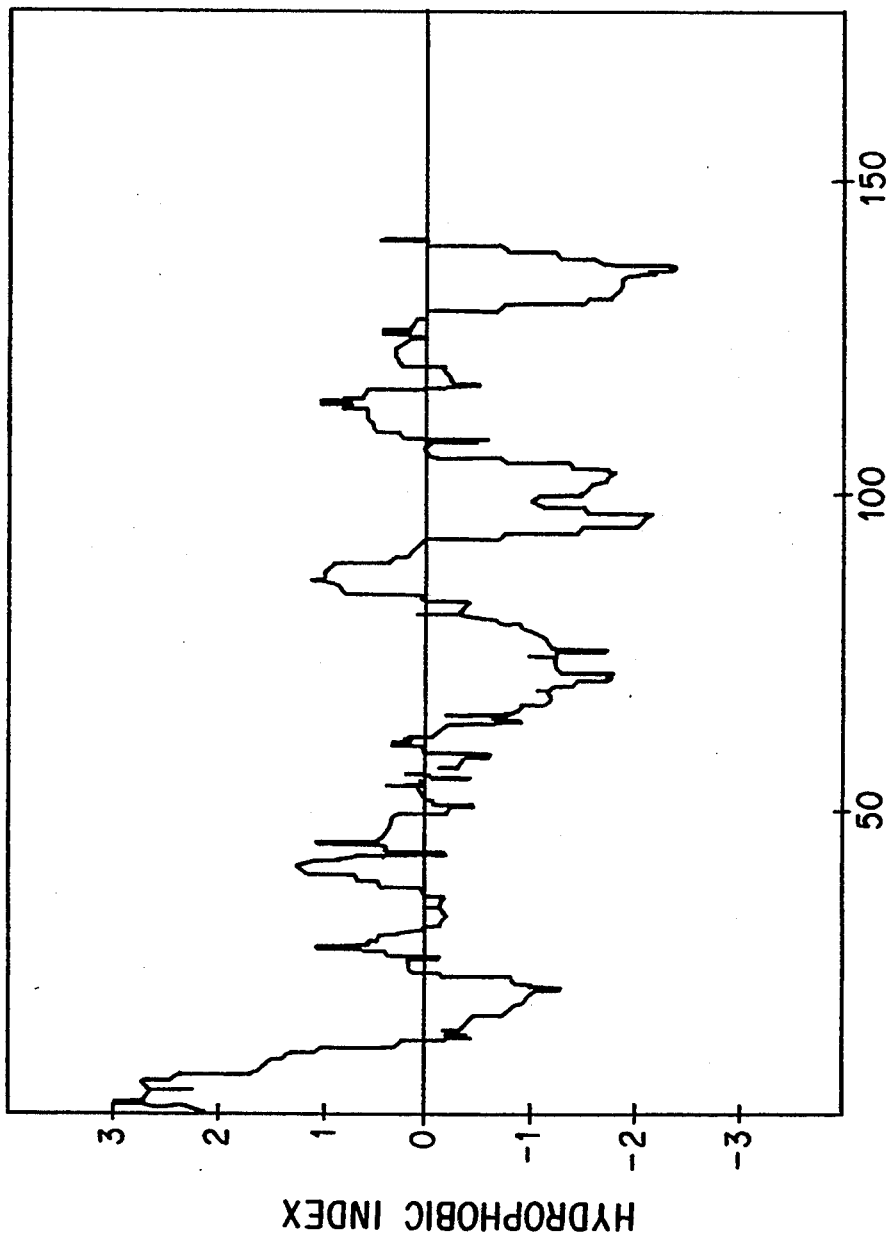

The OV-16 cDNA was excised by digestion with EcoRI and subcloned into the sequencing vector M13mp18 in both orientations. The complete sequence of the antigen-producing clone OV-16 cDNA was determined by the dideoxy chain-termination method (Sanger et al. (1977) Proc. Natl. Acad. Sci. USA 74, 5463–5467). The suggested reading frame used to synthesize the native protein is the same reading frame as in the fusion protein. The nucleotide sequence of cDNA for the low-molecular-weight antigen and the predicted amino acid sequence are shown in FIG. 4A. Sequence analysis of the 813-bp insert revealed an open reading frame encoding 152 amino acids; the size for the OV-16 primary translation product deduced from the cDNA sequence is 16.85 kDa. The assignment of the translational initiation codon 50 bp from the 5' end was made since it was the first ATG in the open reading frame and it contained a purine (adenine) in the −3 position, thought to be a prerequisite for an initiation codon (Kozak, M. (1986) Cell 44, 283–292). The initiation codon is followed by a hydrophobic sequence, predicted by hydropathy analysis (FIG. 4B), highly characteristic of a signal peptide. Using the prediction method of von Heijne (Von Heijne, G. (1986) Nucleic Acids Res. 14, 4683–4690), a potential signal peptidase cleavage site could be found, suggesting cleavage after residue 16 (Gly). The polypeptide is terminated by a TAA stop codon followed by a 3' non-coding region of 307 bp. The 3' non-coding region includes the eukaryotic polyadenylation signal AATAAA, which is located 8 nucleotides from the poly(A) tail (FIG. 4A). There are four potential acceptor tripeptides for N-glycosylation (Asn-Xaa-Ser/Thr) in the predicted amino acid sequence, located in the hydrophilic domains of the protein (boxed areas, FIG. 4A). Glycosylation at these sites could adequately account for the difference between the predicted poly-peptide mass of 16.85 kDa and the observed sizes of the native parasite proteins recognized by the affinity-purified antibodies (24, 26 and 40 kDa).

By hybridization of the nick-translated OV-16 cDNA with the other antigen producing clones, a cross-hybridizing cloned cDNA was detected with a small insert of 682 bp which encoded a hybrid protein of 129 kDa. This cDNA had the same DNA sequence as OV-16 cDNA, but is 131 bp shorter in its 5' region (data not shown).

To determine if there was homology with other proteins, a computer search was conducted (EMBL data bank). There was no homology with other known proteins.

EXAMPLE 5

DNA and RNA Blot Analysis

To identify genomic DNA fragments carrying the gene(s) encoding the parasite antigen OV-16 cDNA, *O. volvulus* DNA was cut with various restriction enzymes, and the resulting fragments were hybridized to the $^{32}$P-labeled cDNA insert of clone OV-16 cDNA. When DNA was cut with the restriction enzyme EcoRI, two bands of 2.5 and 4.3 kb were detected. HindIII digest revealed two bands of 4.3 and 5.0 kb (FIG. 5, left-hand panel, lanes a and b, respectively). No hybridization signals were detected with human DNA from HeLa cells cut with similar restriction enzymes (data not shown).

Figure 5:
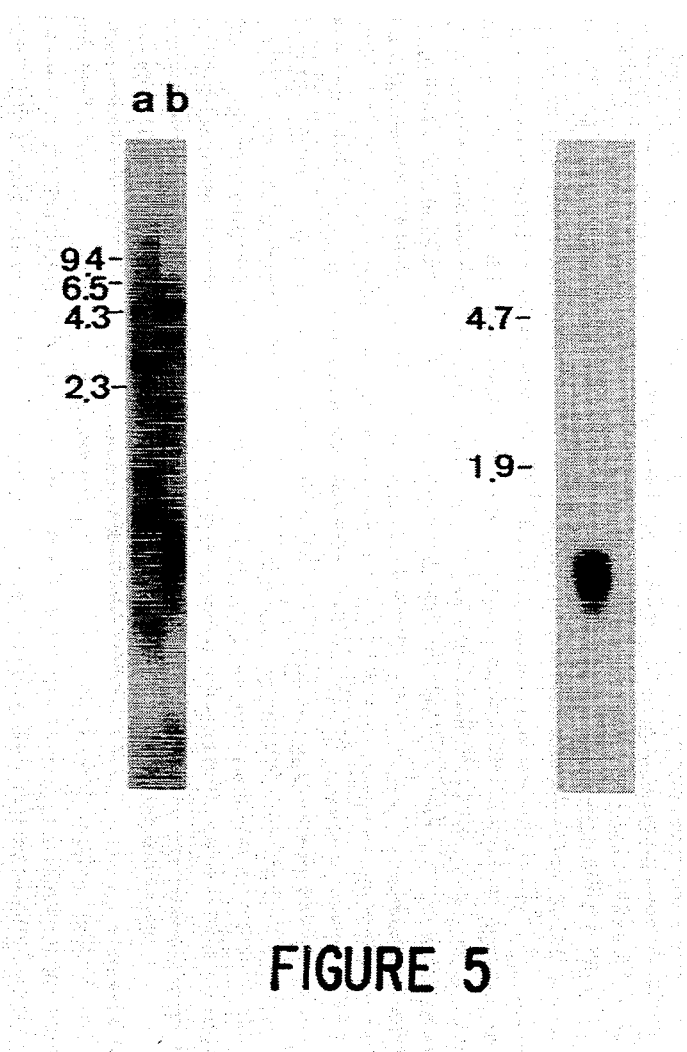

Northern blot analysis for the parasite RNA revealed the presence of a single OV-16 mRNA transcript of 950 nucleotides in length (FIG. 5, right panel).

The data suggest that OV-16 undergoes several post-translational modifications including cleavage of a signal peptide and N-linked glycosylation. A hydropathicity analysis of the polypeptide is reproduced in FIG. 4B. The profile shows a highly hydrophilic polypeptide.

EXAMPLE 6

Immunolocalization of OV-16 cDNA

Figure 6A:
Figure 6B:
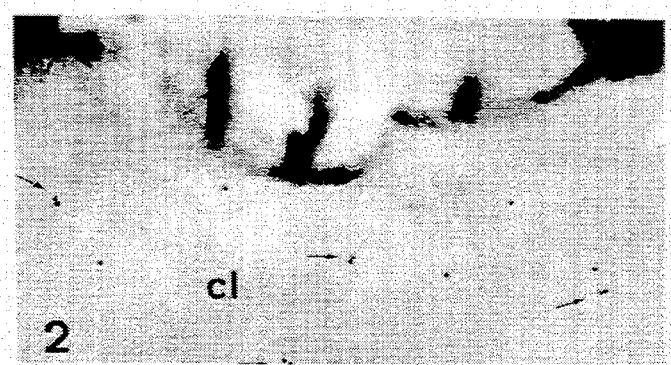
Figure 6C:
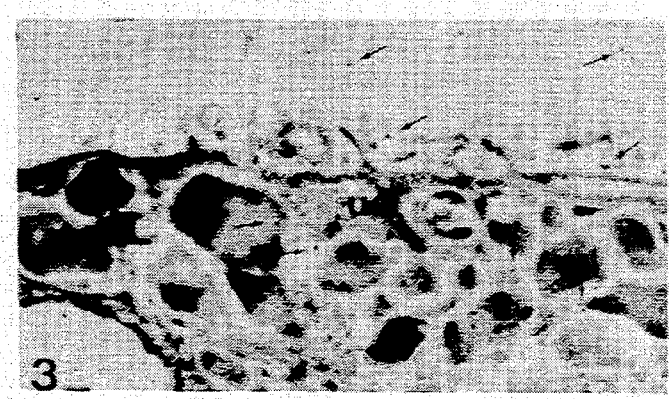

The ultrastructural localization of parasite antigens that share epitopes with the OV-16 cDNA fusion protein was determined by immunoelectron microscopy on thin sections of *O. volvulus* female worms using the affinity-purified anti-OV-16 cDNA antibodies and gold-labeled anti-human IgG (DeMey, J. (1983) Immunogold staining of surface cell antigens in cell suspensions. GAMG 30/colloidal gold coated with immunoglobulins. Jansen Life Science Products Division, Belgium). The antigens were localized in the hypodermis (the cellular layer from which the cuticle of nematodes is derived; FIG. 6.1), the cortical layer of the cuticle (FIG. 6.2), and the apical part and surface of the uterine epithelium (FIG. 6.3).

The subcellular localization and the already-mentioned structural characteristics of the deduced amino acid sequence suggest that OV-16 in its processed form is presented to the host immune system through excretory-secretory mechanisms.

EXAMPLE 7

Purification of OV-16 Fusion Protein

Figure 7:
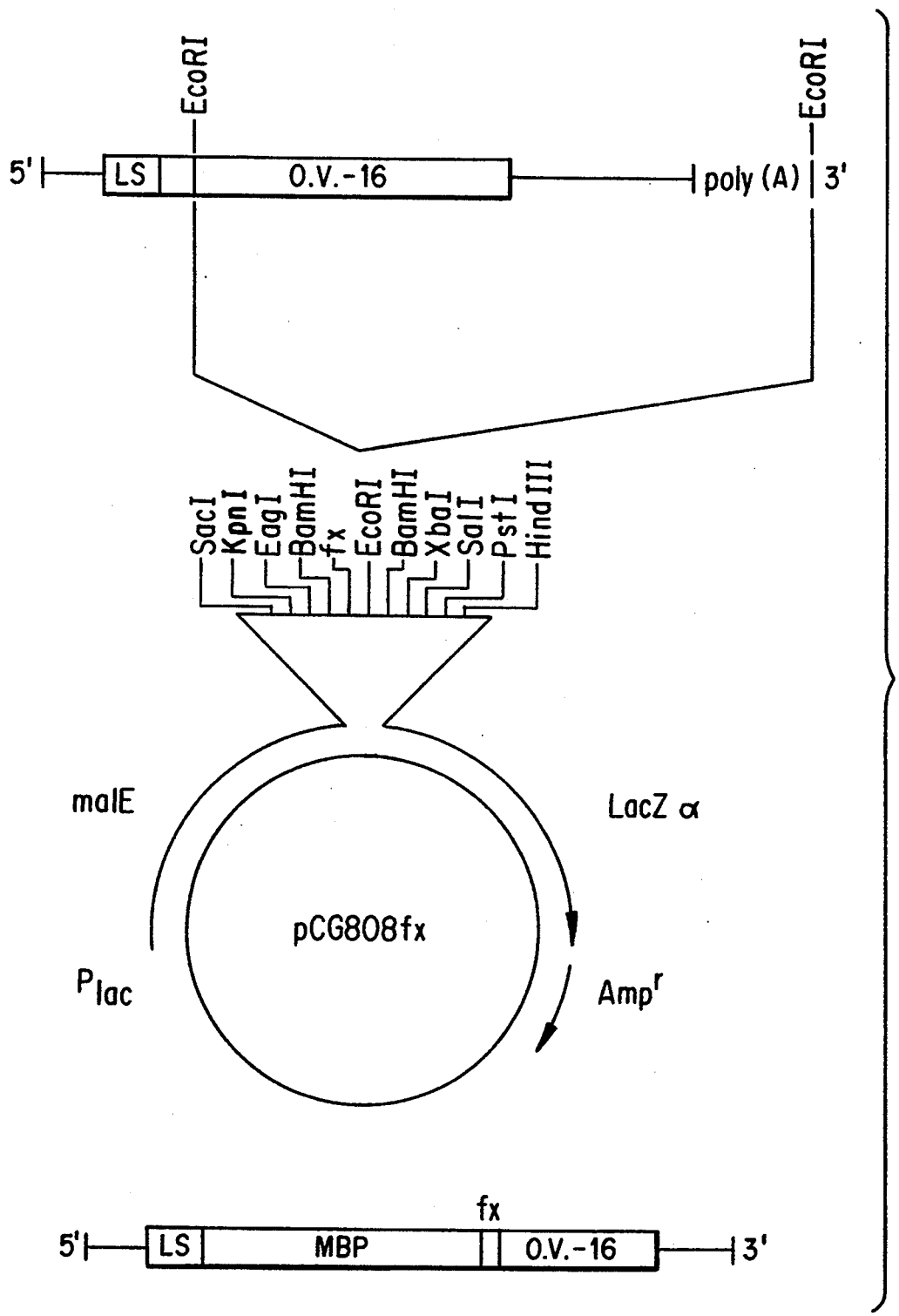

A 682 bp fragment of the OV-16 gene (encoding 123 amino acids) without the leader sequence, was fused to the COOH-terminus of the maltose-binding protein coded for by MaIE of *Escherichia coli* (C. V. Maina et al., Gene 74,365 (1988)). The construction of the recombinant plasmid pCG808fx-16 shown in FIG. 7. The signal peptide was not included in the construct, as efficient synthesis of foreign proteins in *E. coli* often requires deletion of their signal sequences because hydrophobic regions of eukaryotic proteins are toxic to *E. coli* (J. S. Mort et al., Hoppe Seyler Biol. Chem. 369 suppl.,163 (1988); T. Vernet et al., Gene 77,229 (1989)). The purification of the fusion protein MBP-16 is illustrated in FIG. 8 (panel A).

Briefly, *E. coli* 71-18 ([lac-proAM] thi supE [F' pro A+B+ lac$^{Iq}$] lac Z M15) bearing the appropriate plasmid construct was grown at 37° C. in 250 ml Luria broth (LB) to 0.8 O.D. (A 600 nm) and induced with (IPTG) for 2 hr. The cells were harvested by centrifugation at 9 K rpm for 15 min, 4° C. The cell pellet was washed 2x in cold sodium phosphate buffer, pH 7.5 (PBS), 5 mM EGTA, and suspended in 25 ml lysis buffer (10 mM Tris-HCl, pH 7.5, 1 mM phenylmethylsulfonyl fluoride (PMSF), 10 mM β-mercaptoethanol (β-SH), N-tosyl-L-phenylalanine-chloromethyl-ketone (20 μg/ml), leupeptin (10 μg/ml), 20% sucrose, 30 mM NaCl, 10 mM EDTA, 0.2% Tween 20. Cells were lysed by sonication, and unbroken cells and cell debris were removed by centrifugation for 30 min, 4° C. at 10 K rpm. The supernatant was diluted 1:5 with 10 mM Tris-HCl, pH 7.5, 30 mM NaCl, 0.25% Tween 20, 10 mM EDTA, 1 mM PMSF, 10 mM EGTA, and adsorbed overnight at 4° C. with 25 ml cross-linked amylose resin. The bound fusion protein was eluted with maltose, fractions were collected, pooled and dialysed to remove maltose. The dialysate was concentrated and the protein content estimated (C. V. Maina et al., Gene 74,365 (1988), T. Ferenci and U. Klotz, FEBS Lett. 94,213 (1978)). Approximately 6 mg of fusion protein were obtained from 250 ml culture. MBP-16 fusion protein (1 mg) digested with 10 μg factor $X_a$ for 4 days at r.t. resulted in approximately 60–70% of the fusion protein being cleaved. The cleavage products were separated by FPLC using a Mono S ™ column.

Figures 8A, 8B:
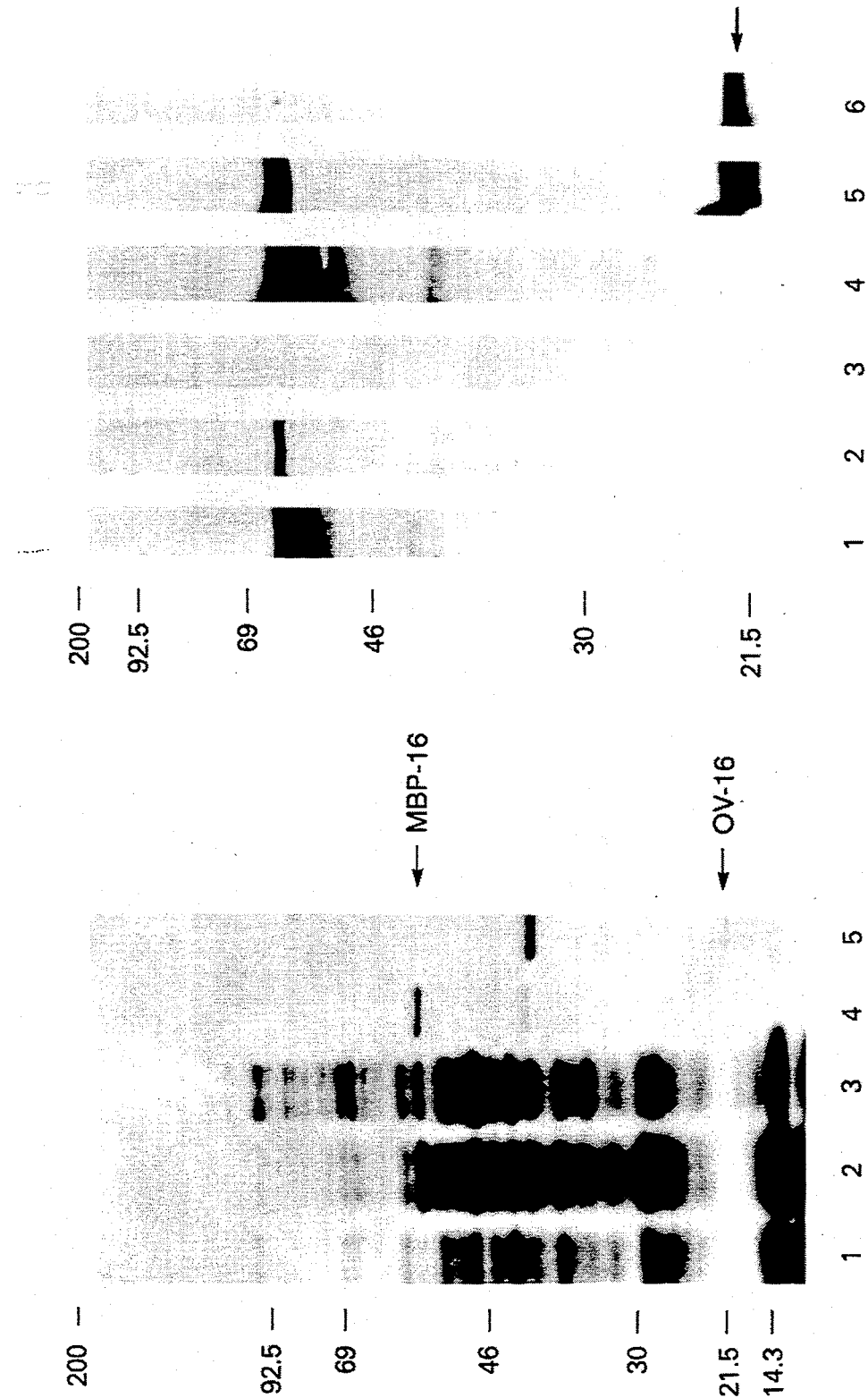

There is a major protein band with a $M_r$ of 52000 which became prominent after induction with 0.3 mM isopropylthiogalactosidase (IPTG) (FIG. 8, lane 2). After the MBP-16 fusion protein is purified by affinity chromatography on cross-linked amylose, the major band at $M_r$ 52000 continues to be present, along with a minor band of $M_r$ 40000 which probably represents a premature termination of the fusion protein or its digestion by *E. coli* proteases (lane 4). As this fusion protein contains the recognition sequence Ile-Glu-Gly-Arg for the protease between the MBP and the OV-16 domains (C. Guan et al., Gene 67,21 (1987); K. Nagai and H. C. Thogersen, Nature 309,810 (1984)), digestion of MBP-16 with activated factor X allowed separation of the two protein domains (panel A, lane 5). Some of the fusion protein remained uncleaved. OV-16 was further purified, from the MBP, the truncated form and the uncut fusion protein, by FPLC using a Mono S ™ column. The purification procedure did not affect antigenicity as determined by immunoblot analysis of the fusion protein and the isolated OV-16 (FIG. 8, panel B).

EXAMPLE 8

Presence of OV-16 in Patients

Figure 9:
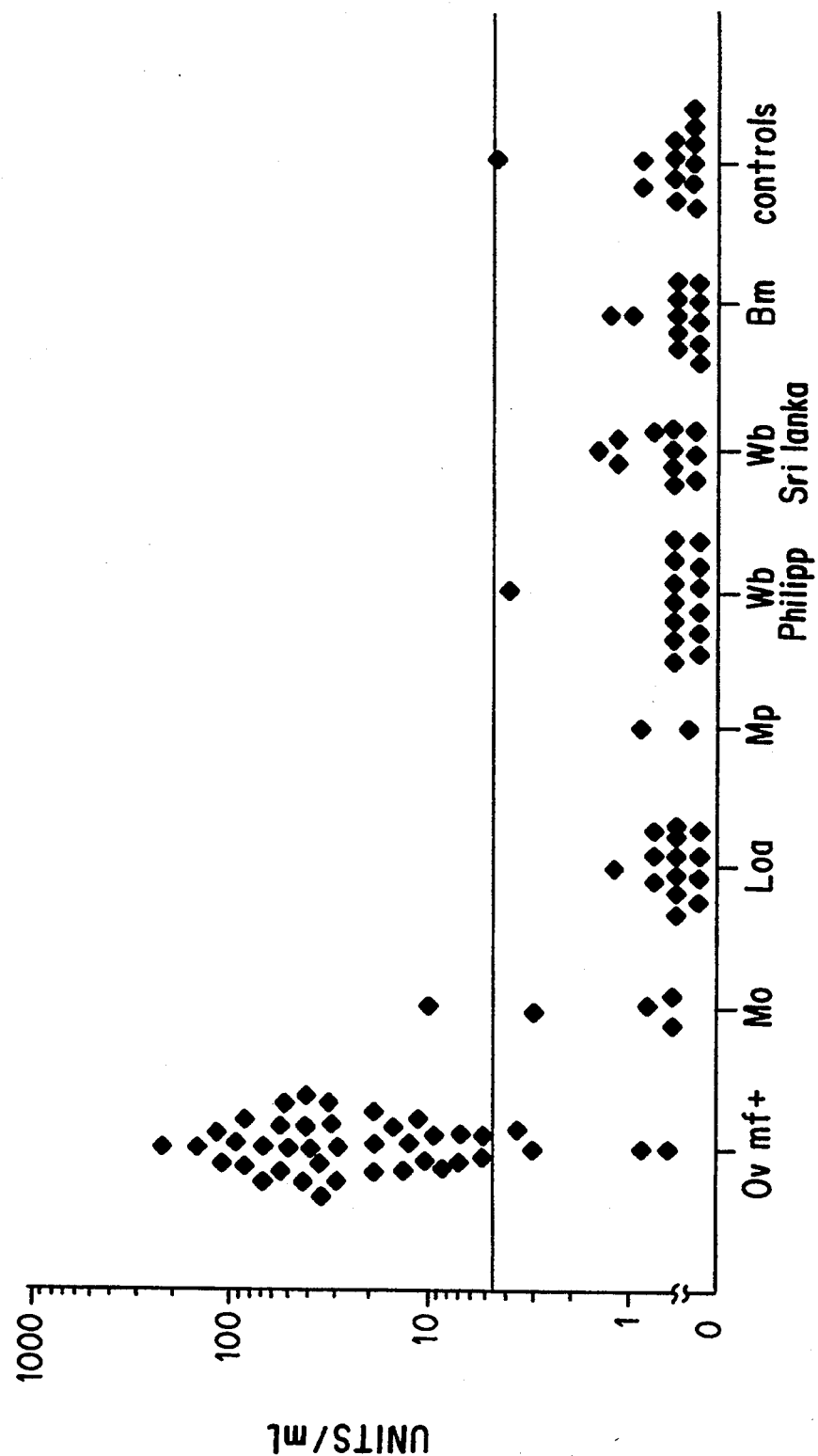

The isolated OV-16 was used in ELISA to analyze the antibody responses of 41 onchocerciasis patients (aged 3–60 years), who had proven infections (mf detected in skin) and were residents of a region highly endemic for *O. volvulus* in the savanna zone of Mali. Onchocerciasis patients were part of a longitudinal study whose detailed parasitological and serological data have been described elsewhere [M. Karam and N. Weiss, Am. J. Trop. Med. Hyg. 40,261 (1985), N. Weiss and M. Karam, Ciba. Found. Symp. 27,180 (1987)]. 'Normal controls' were individuals (Swiss) never exposed to infection with filarial or other nematode parasites of humans. Sera from patients with other filarial infections—*Wuchereria bancrofti, Brugia malayi, Mansonella ozzardi, Loa loa, Mansonella perstans*—and other helminthic infections (K. Nagai and H. C. Thogersen, Nature 309,810 (1984)) were used to ascertain the diagnostic specificity of OV-16 (FIG. 9). Sera from these patients were from either the WHO or NIH Filariasis Serum Banks. Levels of anti-OV-16 antibody were determined by ELISA. Briefly, Immunolon 4 plates (Dynatech, Alexandria, Va.) were coated with 300 ng OV-16 in coating buffer pH 7.6/ml overnight at 4° C. The plates were blocked with 5% BSA for 1 hr at 37° C. All sera were run in duplicate at a 1:100 dilution and incubated overnight. For assays of total IgG, Fc-specific, alkaline phosphatase-conjugated goat antibody to human IgG (Sigma, St. Louis, Mo.) was added. Thirteen uninfected samples were used to determine the normal range (mean ±3 SD). A high-titered standard reference onchocerciasis serum pool was used to generate calibration curves against which all sera were compared for antibody levels (Flow Cytometric Program 1.5, Munich, Germany). Levels are expressed as arbitrary units/ml.

OV-16 allowed for the detection of anti-OV-16 antibodies in 37 of 41 (90%) patients with onchocerciasis (geometric mean 41.4 U/ml [normal<4.6 U/ml]) and was also effective in differentiating onchocerciasis from the other filarial infections, including *L. Loa* (0/14 positive), *W. bancrofti* from the Philippines (0/14 positive) and Sri Lanka (0/11), *B. malayi* from Indonesia (0/12), and *M. perstans* from west Africa (0/2). For *M. ozzardi*, the one individual (of 5 studied) from Venezuela who reacted positively in the ELISA, resided in an area where coinfection with *O. volvulus* was a distinct possibility. Unexposed persons living outside filarial endemic areas (Switzerland) had no antibody to this protein (0/13 positive). Thus, by using this assay, a specificity of 98% (1/57) and a sensitivity of 90% (37/41) for *O. volvulus* was obtained.

No correlation was found between the number of mf per skin snip and the reactivity to OV-16, although there was a decrease in the levels of antibody to OV-16 in microfiladermic patients over 20 years of age (N. Weiss and E. Lobos, unpublished observations), a finding consistent with the modulation of immune responses seen in chronic parasitic infections. While the species-specificity of OV-16 was dramatic (FIG. 9), the antigenicity of OV-16 was also conserved among geographic isolates of *O. volvulus* with patients from the W. African savanna (described here) as well as those from the W.

African rain-forest (Ivory Coast) and from the New World (Guatemala) (E. Lobos and N. Weiss, unpublished observations).

EXAMPLE 9

Humoral Immune Response

Figure 10B:
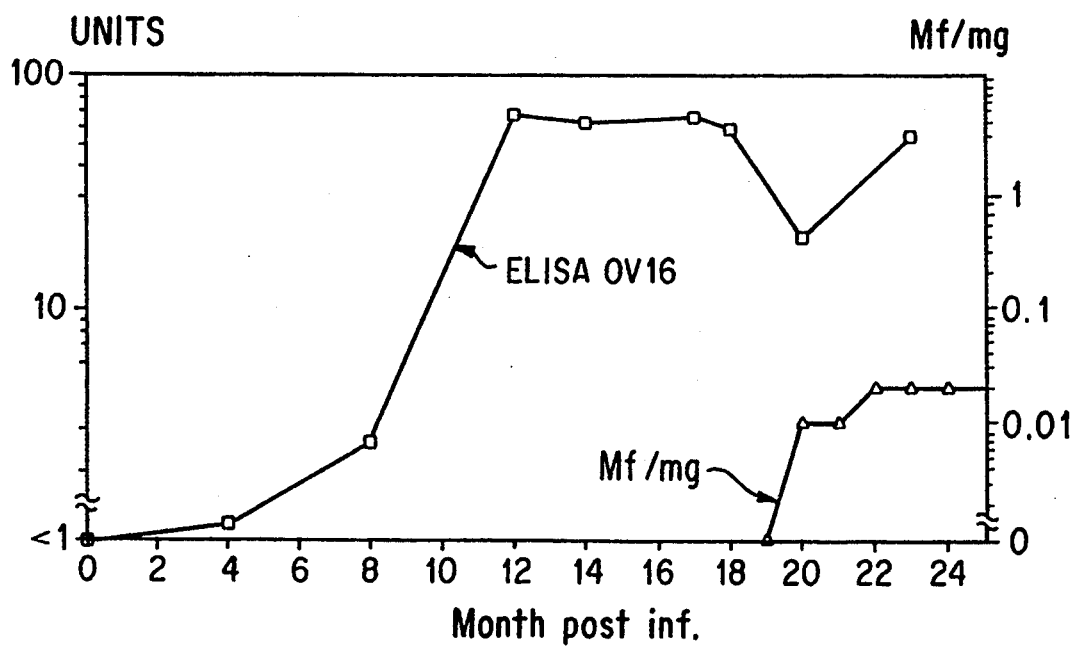
Figure 10A:
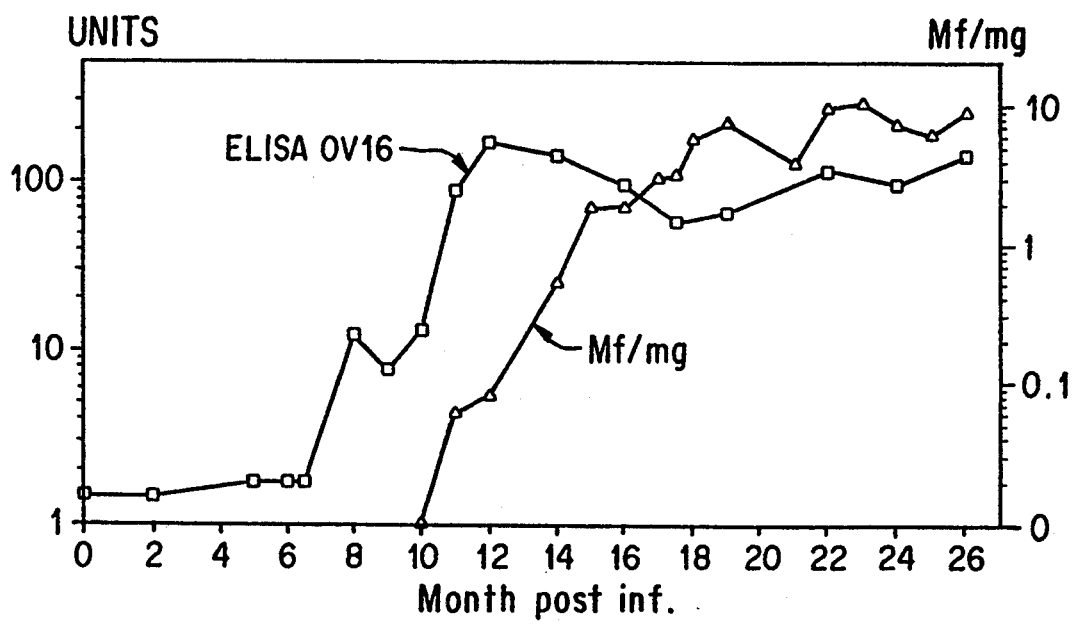

Polyclonal antiserum raised to purified OV-16 demonstrated that OV-16 accumulated in parasite-free culture supernatants in its post-translationally modified forms (E. Lobos, unpublished observations), with $M_r$ in the range 2,000–30,000, and was specifically recognized by the monospecific polyclonal antiserum. This finding suggested that OV-16 is a released parasite product and would be available to induce an immune response early in infection. To examine this possibility more directly, the course of the humoral immune response to OV-16 was monitored in parallel with the onset of patency (first detection of mf in the skin) in two chimpanzees experimentally inoculated with infective Ov larvae (H. R. Taylor et al., Am. J. Trop. Med. Hyg. 39,86 (1988)). FIG. 10 shows that antibodies to OV-16 developed 3 months and 12 months prior to the first appearance of skin mf (FIGS. 10A and 10B).

EXAMPLE 10

Analysis of Parasitologically Negative Children

Because infection of children can be an important epidemiologic indicator of ongoing transmission of *O. volvulus*, the antibody response to OV-16 was analyzed in eight exposed but parasitologically negative children (aged 1–14) who were part of a 4-year longitudinal study carried out in a savanna region of Mali highly endemic for onchocerciasis (Table 1). In three of the children, *O. volvulus* infection could be detected by the presence of antibodies to OV-16, during the prepatent period, 1–1.5 years before the appearance of mf in the skin. In four other children, there was a sharp increase in the antibody to OV-16 in the same year that mf positivity developed. In the eighth patient, no clinical, parasitological or serological evidence of infection was observed and, therefore, he was assumed to be truly uninfected.

TABLE 1*

| | Anti-OV-16 Ab** | | | | | | | |
|---|---|---|---|---|---|---|---|---|
| | microfilariae Year | | | | Skin Year | | | |
| Patient | 0 | 1 | 2 | 3 | 0 | 1 | 2 | 3 |
| 1 | − | + | + | + | − | − | + | + |
| 2 | − | + | + | + | − | − | + | + |
| 3 | + | + | + | + | − | − | + | + |
| 4 | − | + | + | ND | − | + | + | ND |
| 5 | − | + | + | ND | − | + | + | ND |
| 6 | − | − | + | + | − | − | + | + |
| 7 | − | + | + | + | − | + | + | + |
| 8 | − | − | − | − | − | − | − | − |

*Detection of antibodies to OV-16 in children (aged 1–14) from a savanna region in Mali hyperendemic for onchocerciasis. The children were followed during a longitudinal study over 4 years (0 yr, 1 yr, 2 yr, 3 yr), and the data reflect the presence of antibodies to OV-16 in relation to the appearance of skin mf. Patient number 8 remained parasitologically and serologically negative all through the study. Antibody positivity clearly demonstrates the infection at least 1 year before the parasitological diagnosis (patients 1–3). Patients 4–7 showed a sharp increase in antibody level against OV-16 in the same year as the mf appeared.

**A positive value is defined as >3 S.D. above the geometric mean of thirteen normal individuals run simultaneously.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. An isolated nucleotide molecule coding for the polypeptide OV-16 and having the nucleotide sequence set forth in SEQ ID NO: 1.

2. An isolated nucleotide molecule, wherein said nucleotide molecule encodes the amino acid sequence set forth in SEQ ID NO:2.

3. An isolated nucleotide molecule encoding amino acids 30 to 152 set forth in Seq ID NO:2.

4. An isolated nucleotide molecule consisting of nucleotides 139 to 507 set forth in SEQ ID NO: 1.

5. A recombinant DNA molecule comprising a vector and the nucleotide molecule of claim 1.

6. A recombinant DNA molecule comprising a vector and the nucleotide molecule of claim 4.

7. The recombinant DNA molecule of claim 6 wherein said molecule is pCG808fx-16.

8. A cell that contains the recombinant DNA molecule of claim 5.

9. A cell that contains the recombinant DNA molecule of claim 6.

10. A method of producing a polypeptide of OV-16 comprising culturing the cell of claim 8 under conditions such that said nucleotide molecule is expressed and said polypeptide thereby produced., and isolating said polypeptide.

11. A method of producing a polypeptide of OV-16 comprising culturing the cell of claim 9 under conditions such that said nucleotide molecule is expressed and said polypeptide thereby produced, and isolating said polypeptide.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 822 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 52..507

( x i ) SEQUENCE DESCRIPTION: SEQ ID NO:1:

```
CAGTTTGAGG ATCGGTTGCT TGTTTTTGC ATCAATCGTG TATGCTCGAT A ATG CAT      57
                                                         Met His
                                                           1

TGT TTG CAA GTA GTA ATC GCC ATA GTA TTG TAC TCA TTT GGA AAA ATA    105
Cys Leu Gln Val Val Ile Ala Ile Val Leu Tyr Ser Phe Gly Lys Ile
          5              10                 15

TCT GCA GAA AAT GCT AAT TGC AAA AAG TGC ACA CCA ATG TTA GTA GAT    153
Ser Ala Glu Asn Ala Asn Cys Lys Lys Cys Thr Pro Met Leu Val Asp
     20               25                  30

TCG GCA TTC AAG GAA CAT GGA ATT GTA CCG GAC GTT GTA TCA ACA GCT    201
Ser Ala Phe Lys Glu His Gly Ile Val Pro Asp Val Val Ser Thr Ala
 35               40                 45                  50
```

-continued

| | | | | | | | | | | | | | | | | |
|---|---|---|---|---|---|---|---|---|---|---|---|---|---|---|---|---|
| CCT | ACG | AAG | TTG | GTC | AAT | GTT | AGT | TAC | AAT | AAT | CTC | ACG | GTG | AAT | CTG | 249 |
| Pro | Thr | Lys | Leu 55 | Val | Asn | Val | Ser | Tyr 60 | Asn | Asn | Leu | Thr | Val 65 | Asn | Leu | |
| GGC | AAT | GAA | CTT | ACG | CCG | ACG | CAG | GTA | AAG | AAT | CAG | CCG | ACA | AAA | GTA | 297 |
| Gly | Asn | Glu | Leu 70 | Thr | Pro | Thr | Gln | Val 75 | Lys | Asn | Gln | Pro | Thr 80 | Lys | Val | |
| TCA | TGG | GAT | GCG | GAA | CCT | GGA | GCC | TTA | TAT | ACG | CTC | GTT | ATG | ACT | GAT | 345 |
| Ser | Trp | Asp 85 | Ala | Glu | Pro | Gly | Ala | Leu 90 | Tyr | Thr | Leu | Val | Met 95 | Thr | Asp | |
| CCG | GAC | GCA | CCA | TCT | CGA | AAA | AAC | CCC | GTA | TTC | AGA | GAG | TGG | CAC | CAT | 393 |
| Pro | Asp 100 | Ala | Pro | Ser | Arg | Lys 105 | Asn | Pro | Val | Phe | Arg 110 | Glu | Trp | His | His | |
| TGG | TTG | ATA | ATT | AAT | ATT | TCT | GGA | CAA | AAT | GTT | AGC | AGT | GGC | ACA | GTG | 441 |
| Trp 115 | Leu | Ile | Ile | Asn | Ile 120 | Ser | Gly | Gln | Asn | Val 125 | Ser | Ser | Gly | Thr | Val 130 | |
| TTA | TCT | GAT | TAT | TGG | ATC | AGG | TCC | ACG | AAA | AGG | CAC | AGG | ACT | TCA | TCG | 489 |
| Leu | Ser | Asp | Tyr | Trp 135 | Ile | Arg | Ser | Thr | Lys 140 | Arg | His | Arg | Thr | Ser 145 | Ser | |
| TTA | TGT | ATT | CTT | GGT | TTA | TAAACAACCT | | GGAAGTATCA | | CGGATACTCA | | | | | | 537 |
| Leu | Cys | Ile | Leu 150 | Gly | Leu | | | | | | | | | | | |

| | |
|---|---|
| ACATGGCGGA AATCGCCGAA ATTTCAAAGT TATGGATTTT GCAAACAAAC ATCACTTGGG | 597 |
| AAATCCAGTT GCCGGAAACT TCTTCCAGGC TAAACATGAG GATTAACATG AAGACTGTGA | 657 |
| ATATGAATAT GAACTGCTTG AACGACACTA GAGACTCAGC GACTGATACT TATTGATTTG | 717 |
| TTTTTGTAAC ATTGAATGA ATTTTTCTTT ACAGTTATTT GCTAAATTTC GAATTTAATG | 777 |
| GGAATAAATA TTTTTTAAAA AAAAAAAAA AAAAAAGGA ATTCC | 822 |

( 2 ) INFORMATION FOR SEQ ID NO:2:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | His | Cys | Leu | Gln 5 | Val | Val | Ile | Ala | Ile 10 | Val | Leu | Tyr | Ser | Phe Gly 15 |
| Lys | Ile | Ser | Ala 20 | Glu | Asn | Ala | Asn | Cys 25 | Lys | Lys | Cys | Thr | Pro 30 | Met Leu |
| Val | Asp | Ser 35 | Ala | Phe | Lys | Glu | His 40 | Gly | Ile | Val | Pro | Asp 45 | Val | Val Ser |
| Thr | Ala 50 | Pro | Thr | Lys | Leu | Val 55 | Asn | Val | Ser | Tyr | Asn 60 | Asn | Leu | Thr Val |
| Asn 65 | Leu | Gly | Asn | Glu | Leu 70 | Thr | Pro | Thr | Gln | Val 75 | Lys | Asn | Gln | Pro Thr 80 |
| Lys | Val | Ser | Trp | Asp 85 | Ala | Glu | Pro | Gly | Ala 90 | Leu | Tyr | Thr | Leu | Val Met 95 |
| Thr | Asp | Pro | Asp 100 | Ala | Pro | Ser | Arg | Lys 105 | Asn | Pro | Val | Phe | Arg 110 | Glu Trp |
| His | His | Trp 115 | Leu | Ile | Ile | Asn | Ile 120 | Ser | Gly | Gln | Asn | Val 125 | Ser | Ser Gly |
| Thr | Val 130 | Leu | Ser | Asp | Tyr | Trp 135 | Ile | Arg | Ser | Thr | Lys 140 | Arg | His | Arg Thr |
| Ser 145 | Ser | Leu | Cys | Ile | Leu 150 | Gly | Leu | | | | | | | |